United States Patent [19]
Boyd et al.

[11] Patent Number: 5,361,643
[45] Date of Patent: Nov. 8, 1994

[54] LPG SAMPLING SYSTEM

[75] Inventors: Charles R. Boyd, Victoria; John D. Anderson, Lake Jackson, both of Tex.

[73] Assignee: Texas Sampling Co., Victoria, Tex.

[21] Appl. No.: 100,129

[22] Filed: Jul. 30, 1993

[51] Int. Cl.$^5$ .............................................. G01N 1/10
[52] U.S. Cl. .................................................. 73/863.71
[58] Field of Search ... 73/863.71, 863, 863.01–863.02, 73/863.31–863.33, 863.41, 863.51, 863.57–863.58, 863.72–863.73, 863.81–863.83, 863.85–863.86, 864, 864.41, 864.51–864.52, 864.63

[56] References Cited

U.S. PATENT DOCUMENTS

| | | | |
|---|---|---|---|
| 258,872 | 6/1882 | Ashcroft | 340/624 |
| 3,166,939 | 1/1965 | Koeller. | |
| 3,241,372 | 3/1966 | Maxwell | 73/863.51 |
| 3,429,186 | 2/1969 | Price et al. | 73/863.61 |
| 3,638,476 | 2/1972 | Paterson et al. | 73/863.51 |
| 4,194,398 | 3/1980 | Gastrock. | |
| 4,272,483 | 6/1991 | Schick. | |
| 4,712,434 | 12/1987 | Herwig. | |
| 4,755,357 | 7/1988 | Noguchi. | |
| 4,800,761 | 1/1989 | Spencer. | |
| 4,987,785 | 1/1991 | Spencer. | |
| 5,116,330 | 5/1992 | Spencer | 73/863.71 |
| 5,131,282 | 7/1992 | Kuhner. | |

*Primary Examiner*—Hezron E. Williams
*Assistant Examiner*—Daniel S. Larkin
*Attorney, Agent, or Firm*—Pravel, Hewitt, Kimball & Krieger

[57] ABSTRACT

This invention relates to a sampling system for collecting a sample in a sample cylinder having valves on both ends. The system includes an inlet line, a return line, a four-way valve, a level indicator and a sample loop including sample cylinder connections. After the sample cylinder is connected to the sample cylinder connections, the system and four-way valve allow the sample fluid to be selectively routed to flow in the inlet line, through the sample loop and sample cylinder and through the exit line or to flow in the inlet line and through the exit line, bypassing the sample loop.

12 Claims, 2 Drawing Sheets

LPG SAMPLING SYSTEM

BACKGROUND OF THE INVENTION

1. Field of the Invention

This invention relates to a sampling system for collecting a sample in a sample cylinder having valves on both ends. More particularly, this system provides a loop including sample cylinder connections and a level indicator. In use, a sample cylinder is placed in the connections and the fluid is allowed to flow through the loop until the loop is liquid-filled and contains a representative sample. Then, the flow is diverted from the loop. Fluid is removed from the loop to lower the pressure in the loop, thus vaporizing the liquid. This continues until a vapor-liquid interface is obtained in the sample cylinder as indicated by the level indicator. When this occurs, the valves at both ends of the sample cylinder are closed to isolate the sample contained in the sample cylinder.

2. Description of the Related Art

In the operation of many chemical and other processes, it is often necessary to periodically sample fluids which are flowing within the process at various points. For a variety of reasons, it is often advantageous to collect the fluid in a sample cylinder having valves on both ends. A sample cylinder having valves on both ends is particularly applicable for obtaining samples of liquids having high vapor pressure. Hydrocarbon liquid samples, e.g., LPG (liquified petroleum gas) and butane, are frequently caught in sample cylinders having valves on both ends.

When collecting a liquid sample in a sample cylinder having valves on both ends, it is known to vent the cylinder to provide a vapor space in the cylinder to prevent rupture due to liquid expansion in a liquid filled cylinder, e.g., upon an increase in temperature.

The known systems and methods for collecting a sample in a sample cylinder having valves on both ends presents several disadvantages. First, many known systems and methods require excessive venting of sample material to the atmosphere to achieve a representative sample in the sample cylinder and/or to achieve a vapor space in the sample cylinder. This venting of sample material results in health concerns in that the person catching the sample is exposed to the sample material and environmental concerns due to contamination of the air, and in some cases, the soil or water runoff. Also, known systems for the collection of a sample in a sample cylinder having valves on both ends typically require the operation of several valves. This may lead to errors in collecting a representative sample and is time consuming as it requires special procedures.

U.S. Pat. No. 4,712,434 to Herwig discloses a sample system for capturing a sample in a sample cylinder having valves on both ends. The system includes a 4-way tap from which leads two lines, which can be connected together from and to the sample source and to other lines which can be connected together which lead to a sample cylinder having valves on both ends. The system further includes a supply line for an inert gaseous flushing medium which joins the line leading into the sample cylinder, and a discharge line for the inert flushing medium, which leads from the line coming out of the sample cylinder and proceeds to a disposal system. In use, the system and sample cylinder are first flushed with an inert gaseous flushing medium with the flushing medium being routed to the discharge line and disposal system. Then, a predetermined volume of the inert gaseous flushing medium is captured between two valves in the discharge line. Next, the four-way tap is positioned to allow the sample to flow through the system and sample cylinder. Then, the four-way tap is positioned so as to isolate the sample cylinder. Next, the valve in the discharge line closest to the sample cylinder is opened to allow the inert gaseous flushing medium to enter into the system and sample cylinder so as to provide a vapor space in the sample cylinder.

There are several disadvantages to the system and method disclosed in U.S. Pat. No. 4,712,434 to Herwig. First, the system must be flushed with the inert gaseous medium prior to collecting the sample in the sample cylinder. This flushing is disadvantageous for several reasons. As it includes several steps, it may take considerable time to flush the system and collect the sample. Also, due to the required number of steps, it may lead to operator error which may result in accidental release of sample or inert gaseous flushing medium. Also, due to the volume of flushing material, the system may be costly to operate or require special disposal facilities. Second, by using an inert gaseous flushing medium to obtain the vapor space in the sample cylinder, the sample cylinder may become "contaminated" with the inert gaseous flushing medium. This presents a problem, especially for LPG sampling, because the level of "inerts" within a production sample is an important measurement, as an increased level of inerts present may subsequently raise the pressure of storage facilities, resulting in venting of the storage facilities or over-pressuring the storage facilities. Third, this system is difficult to operate in that the technician (person collecting sample) cannot easily determine whether the system is operating correctly. This may lead to the collection of a non-representative sample or the sending of excessive sample and vent material to the disposal system.

U.S. Pat. No. 5,131,282 to Kuhner discloses a system for collecting a sample in a sample cylinder having valves on both ends, the system having two three-way valves, with each valve of the sample cylinder being connected to a three-way valve. Here, each three-way valve has three positions, i.e., a sample position, a vent position, and an off position. With this number of operating variables, the system is complicated and requires several steps to operate. This could lead to operator error in relation to collecting a representative sample or accidentally releasing material to the atmosphere which may result in health or environmental concerns. Also, this system does not provide a satisfactory means for obtaining a vapor space in the sample cylinder without venting the sample cylinder to the atmosphere.

Thus, there exists a need for a sampling system for collecting a sample in a sample cylinder having valves on both ends which allows quick, easy, and uncomplicated collection of the sample, and which allows a technician to easily and accurately determine that the system is operating correctly.

SUMMARY OF THE INVENTION

The invention relates to a sampling system for collecting a sample in a sample cylinder having valves at both ends. This system includes an inlet line, a return line, a four-way valve having two flow channels, a sample loop including sample cylinder connections, a level indicator for indicating the level in the sample cylinder, and a vent line from the sample loop.

With the present invention, the fluid to be sampled normally flows in the inlet line, through a first channel of the four-way valve and exits through the return line. When it is desired to obtain a sample, the technician positions the four-way valve such that the fluid flows in the inlet line, through the first channel of the four-way valve, enters the sample loop including the sample cylinder having valves on both ends, then continues through the sample loop, exiting the sample loop through the second channel and exiting through the return line. The fluid is allowed to flow in this path until the sample loop is completely liquid filled and contains a representative sample. Then, the technician positions the valve to the first position, i.e., such that the fluid flows in the inlet line through the first channel and exits through the return line. He then uses the vent line to remove liquid from the sample loop such that the sample will be subjected to a reduced pressure, causing vaporization of the sample which provides a vapor space in the sample cylinder, the level in the cylinder being indicated by the level indicator. At this point, the valves on both ends of the cylinder are closed, the sample loop is completely vented, and the sample cylinder may be removed.

The present invention is simple and easy to operate since the technician need only operate two valves, i.e., the four-way valve and the vent valve. Also, due to the configuration of the system with the sight glass or other level indicator indicating the level in the sample cylinder, the technician is easily and accurately assured that the system is operating correctly. He can see the sample loop filling with liquid, the fluid circulating through the loop, and then, upon venting, he can see the level in the sample cylinder to assure a vapor space is achieved.

BRIEF DESCRIPTION OF THE DRAWINGS

A better understanding of the present invention can be obtained from the detailed description of exemplary embodiments set forth below is considered in conjunction with the attached drawings in which.

DETAILED DESCRIPTION OF THE PREFERRED EMBODIMENTS

Figure 1:
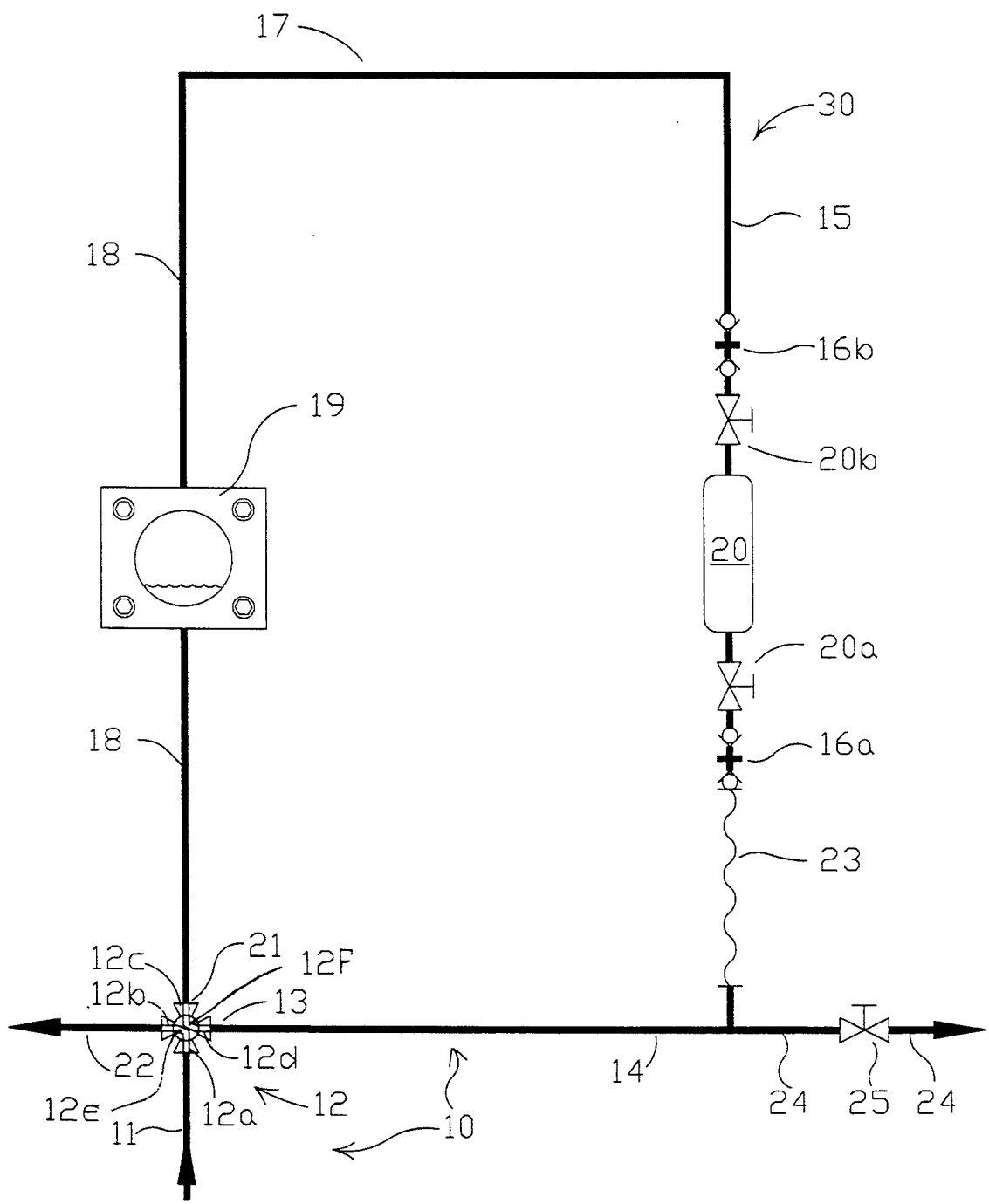
FIG. 1 is a process flow diagram showing the preferred embodiment of the sampling system of the present invention.

The present invention relates to a sampling system for collecting a sample in a sample cylinder having valves on both ends. FIG. 1 shows one embodiment of a system 10 for collecting a sample in a sample cylinder 20 having valves at both ends 20a, 20b. The system is composed of 6 main components: (1) an inlet line 11, (2) a four-way valve 12, (3) a sample loop 30 having sample cylinder connections 16a, 16b, (4) a level indicator 19 for indicating the level in the sample cylinder 20, (5) a return line 22, and (6) a vent line 24 for removing sample material from the sample loop.

Four-way valve 12 is preferably a ball valve having dual flow channels 12e, 12f, each channel 12e, 12f generally L-shaped. When a sample is not being caught, i.e., bypass operation, valve 12 is positioned such that one flow channel 12e connects port 12a with port 12b, while a second L-shaped channel 12f connects port 12c with 12d. With the valve 12 positioned in this manner, sample flows in the inlet line 11, through port 12a, through the first L-shaped channel 12e, exiting through port 12b and return line 22.

To obtain a sample, as discussed below, the technician would rotate valve 12 by 90°, such that the first L-shaped channel 12e would connect port 12a with port 12d and the second L-shaped channel 12f would connect port 12b with port 12c. While valve 12 is preferably a ball valve having dual L-shaped channels 12e, 12f, valve 12 may be any type of valve suitable for achieving the operation described above.

The sample loop 30 consists of piping or tubing to route the sample fluid from inlet point 13 at port 12d, through a sample cylinder 20, through the level indicator 19 and exiting the sample loop 30 at outlet point 21 at port 12c. The sample loop 30 contains two sample cylinder connections 16a, 16b for connecting to the valves 20a, 20b on both ends of the sample cylinder 20. To prepare the sample loop 30 for collecting a sample, the technician need only connect a sample cylinder 20 to the sample cylinder connections 16a, 16b and open sample cylinder valves 20a, 20b. Preferably, as part of the loop sample cylinder leg 15, the sample loop 30 contains a flexible hose 23 designed to facilitate connection of the sample cylinder 20 to the sample loop 30. Flexible hose 23 may also be used to allow the collection of a sample in various sized sample cylinders 20.

Normally, when a sample is not being obtained, the sample fluid flows in inlet line 11, through port 12a through a first L-shaped channel 10c, exiting port 12b and return line 22. When a sample is desired to be obtained, the technician rotates valve 12 such that the flow is routed through one L-shaped channel 12c from port 12a to port 12d, entering sample loop 30 at an inlet point 13. The sample fluid then flows in inlet line 11, through port 12a, through port 12d, and enters sample loop 30 at inlet point 13. The flow continues through loop bottom leg 14 and through loop sample cylinder leg 15, which contains flexible hose 23 and the sample cylinder connections 16a, 16b. The sample fluid fills and flows through the sample cylinder 20, flows through loop top leg 17, through loop level indicator leg 18, through level indicator 19, exiting sample loop 30 at outlet point 21. The fluid continues to flow through port 12c, through the second L-shaped channel 12f and exits through port 12b and return line 22.

As discussed below, when the sample fluid is first routed to the sample loop 30, the sample loop 30 will generally be at a low pressure, i.e., approximately 5 to 50 psig. Thus, when the fluid to be sampled is LPG, there is considerable vaporization upon first diverting the sample to the sample loop 30. The LPG is allowed to flow through the sample loop 30 for a sufficient amount of time to allow the sample loop 30 to become liquid filled and for a sufficient amount of time to obtain a representative sample in the sample loop 30. After the sample fluid has flowed in the path as described above for a sufficient amount of time to allow the sample loop 30 to become liquid filled and to obtain a representative sample, valve 12 is rotated 90°, such that the a first L-shaped channel 12e connects port 12a with port 12b and the second L-shaped channel 12f connects port 12c with port 12d. This in effect allows sample fluid to bypass the sample loop 30 since it flows from inlet line 11 through port 12a, through port 12b, and exits through return line 22.

Manipulation of valve 12 in the above stated manner also isolates the sample fluid which is contained in the sample loop 30 and sample cylinder 20 from the inlet line 11 and the return line 22. Also, this manipulation fluidly connects port 12c with port 12d through one of the L-shaped channels 12f. Once the sample is isolated or captured in the sample loop 30, the technician then manipulates vent valve 25 to allow liquid sample to be vented from sample loop 30. Vent line 24 and vent valve 25 are preferably located at a position below sample cylinder 20 and level indicator 19. Vent line 24 and vent valve 25 may preferably be located on either loop level indicator leg 18, loop bottom leg 14, or loop sample cylinder leg 15. When vent valve 25 is opened to allow liquid sample to flow from sample loop 30 to a flare or other disposal system (not shown), the pressure in the sample loop 30 is reduced, and the sample begins to vaporize. Liquid sample is removed through vent line 24 and vent valve 25 until the vapor-liquid interface, i.e., the level, is located within the sample cylinder 20 as shown by level indicator 19.

Once the sample cylinder 20 contains a level, i.e., sample cylinder 20 has a vapor space, the technician closes valve 25 and then the valves 20a, 20b on both ends of the sample cylinder 20 so as to isolate the sample fluid within the sample cylinder 20. Next, vent valve 25 is opened such that the sample loop 30 is vented to a low pressure, e.g. 5 to 10 psig. At this point, it is safe, both from a health and environmental aspect, to remove the sample cylinder 20 by disconnecting valves 20a, 20b from sample cylinder connections 16a, 16b.

The sample cylinder connections 16a, 16b are preferably quick connect connections.

Figure 2:
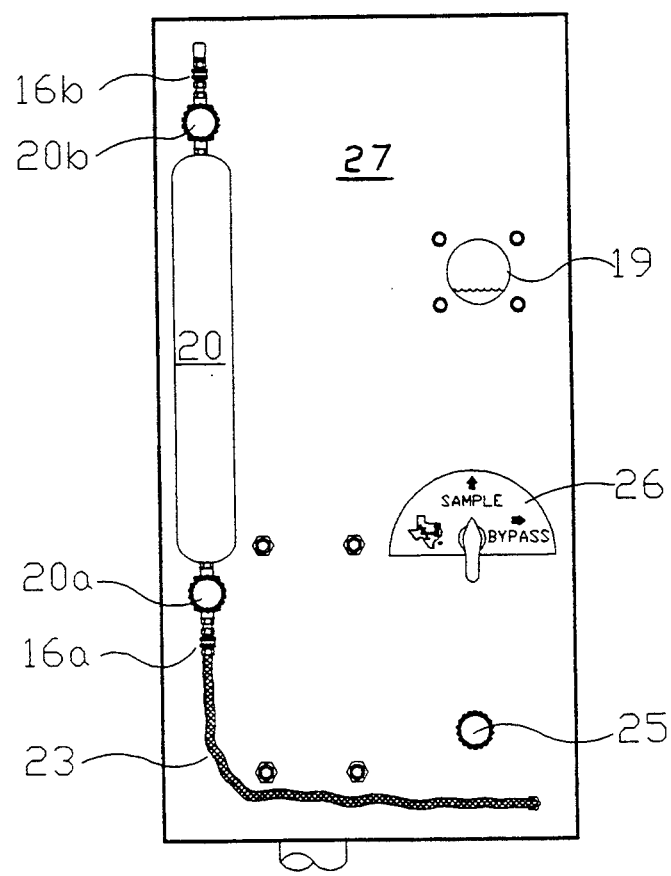
FIG. 2 is a front view of the sampling system of FIG. 1 installed on a mounting plate.
Figure 3:
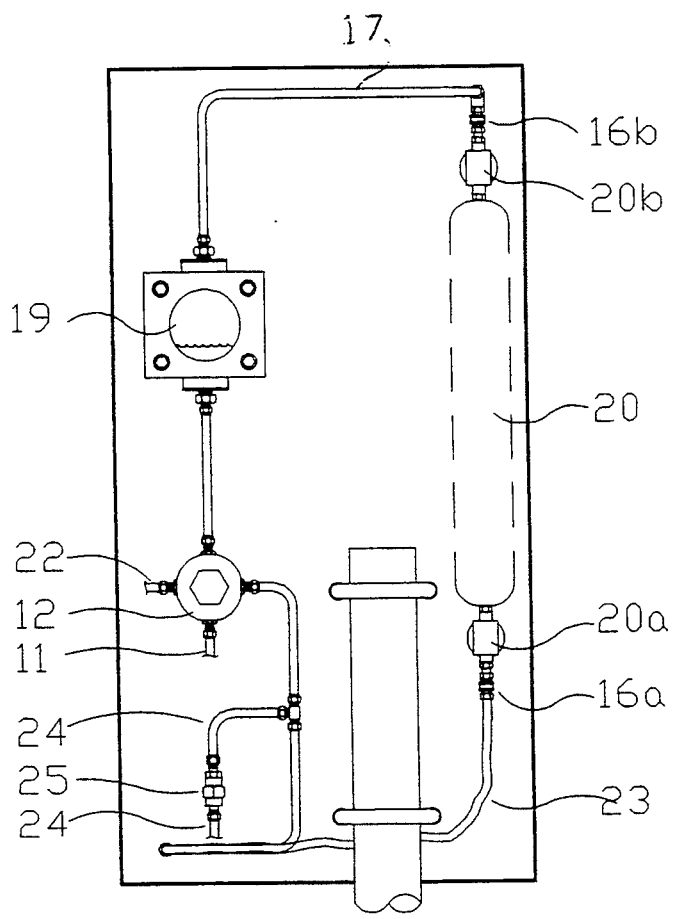
FIG. 3 is a back view of the sampling system of FIG. 1 installed on a mounting plate.

The "level indication means" 19 may be any known method of or apparatus for indicating a level in the sample cylinder 20. Preferably, level indication means 19 is a sight glass 19. As depicted in FIGS. 1, 2 and 3, preferably, sight glass 19 is located in the same vertical position as sample cylinder 20 such that the level of sample cylinder 20 is visually indicated in the sight glass 19. This embodiment is preferable in that it is easy to use and gives the technician visual assurance that the system 10 is operating correctly. Also, a sight glass 19 is preferred as it allows the technician to visually watch the sample loop 30 fill with liquid and the liquid flow through the system 10 to assure that a representative sample is obtained. While less preferred, other level indication means 19 may be used, e.g., ball floats, differential pressure level indicators, or magnetic coupled float indicators. These level indication means are less preferred since they do not give the technician visual assurance that the system 10 is operating correctly through all phases of collecting the sample.

"Loop means for providing fluid communication between the four-way valve, the sample cylinder and the level indication means" is preferably piping or tubing which provides fluid communication between these elements as shown in FIG. 1. However, it is intended that this loop means include any other means for providing fluid communication between these elements.

The "venting means" is preferably vent line 24 and vent valve 25, which allow the sample loop 30 to be vented, e.g., to a disposal system. Venting means may be any known method of or apparatus for removing sample liquid from the sample loop 30 such that a level is obtained in sample cylinder 20 so as to provide the vapor space.

Preferably, the valve 12 has a corresponding position indicator 26 (see FIG. 2) to indicate whether the fluid from the inlet line 11 is flowing into the sample loop 30 or bypassing the sample loop 30 and flowing through return line 22. Preferably, the position indicator 26 has two indicated positions, e.g., "sample" and "bypass", to provide increased ease of operation and reduce the possibility of operator error in operating the system 10.

FIGS. 2 and 3 show the system 10 mounted on a mounting plate 27 with the sample cylinder 20 located in a vertical position. While FIGS. 2 and 3 show the preferred mounting, any convenient mounting may be used.

This system 10 has the advantage that it allows the use of either sample cylinders having "outage tubes" or sample cylinders without outage tubes. An "outage tube" or "dip tube" is a short section of tubing internally fixed to a sample cylinder at one of the valves on the end of the sample cylinder, which allows for the obtaining of a vapor space upon opening the valve to vent the cylinder. Also, with many known systems, the outage tube was required to be positioned in an upright position. With the present system 10, if the sample cylinder contains an outage tube, it can be installed in either position, i.e., upright or in a downwards position. Thus, the present system may be used with the operating facility's existing stock of sample cylinders regardless of whether they have outage tubes or not. Also, there is no operator error associated with installing the outage tube in an improper position.

Modifications may be made to the system 10 which do not deviate from the claimed invention. For example, though it is preferred that sample cylinder 20 be mounted in a vertical position, it may be located in any horizontal or vertical position which will allow the level indicator 19 to detect a level in the sample cylinder 20 so as to provide the vapor space. Also, though it is preferred that valve 12 be a ball valve, any valve having two flow channels 12e, 12f so as to accomplish the functions stated above may be used.

The system 10 solves the problems mentioned above by providing a sampling system which does not require excessive venting of sample material to the atmosphere to achieve a representative sample in the sample cylinder or to achieve a vapor space in the sample cylinder. Also, the system 10 provides a sampling system which is easy to operate and provides assurance that the system is operating correctly so as to facilitate obtaining a representative sample while ensuring that there are no operator errors.

Although the invention has been described with reference to its preferred embodiments, those of skill in the art may from this description appreciate changes and modifications which can be made therein which do not depart from the scope and spirit of the invention as described and claimed hereafter.

We claim:

1. A sampling system for collecting a sample in a sample cylinder having valves on both ends, comprising:
   an inlet line;
   a return line;
   a four-way valve having a first flow channel and a second flow channel;
   level indication means for the direct indication of a level in the sample cylinder;
   loop means for providing fluid communication between the four-way valve, the sample cylinder and the level indication means, said loop means having an inlet point and an outlet point;
   venting means to vent from the loop means;

wherein the four-way valve is selectively positionable between a first position, wherein the first flow channel provides fluid communication between the inlet line and the return line and the second flow channel provides fluid communication between the inlet point of the loop means and the outlet point of the loop means, and a second position, wherein the first flow channel provides fluid communication between the inlet line and the inlet point of the loop means and the second flow channel provides fluid communication between the outlet point of the loop means and the return line.

2. The sampling system of claim 1, wherein the loop means includes at least two sample cylinder connections for installing the sample cylinder having valves on both ends into the loop means.

3. The sampling system of claim 2, wherein the loop means includes flexible tubing to facilitate connecting and disconnecting the sample cylinder having valves on both ends with the sample cylinder connections.

4. The sampling system of claim 1, wherein the level indication means is a sight glass.

5. The sampling system of claim 4, wherein the loop means is constructed so as to locate the sight glass at a position so as to indicate a level in the sample cylinder.

6. The sampling system of claim 1, wherein the loop means comprises tubing to connect the four-way valve, the sample cylinder, and the level indication means.

7. The sampling system of claim 6, wherein the loop means is constructed such that the sample cylinder is oriented at least partially vertically.

8. The sampling system of claim 6, wherein the loop means is constructed such that the sample cylinder is oriented vertically.

9. The sampling system of claim 1, wherein the venting means comprises a vent line and a vent valve.

10. The sampling system of claim 1, further comprising indicating means for indicating the position of the four-way valve.

11. A method for collecting a sample of a fluid from a sample line into a sample cylinder having valves on both ends, the method comprising the steps of:
   selecting a sampling system having:
      a four-way valve having a first port and a second port;
      a loop having at least two sample cylinder connections, an inlet point and an outlet point, the inlet point fluidly connected with the first port and the outlet point fluidly connected with the second port and;
      a level indicator for direct indication of a level in the sample cylinder, and
      a vent;
   installing a sample cylinder in the sample cylinder connections;
   positioning the four-way valve to allow the fluid to flow in the inlet point, through the loop, and out the outlet point;
   allowing the fluid to flow in the loop so as to liquid-fill the loop; venting fluid from the loop to lower the pressure in the loop to cause vaporization of the liquid;
   closing the valves on both ends of the sample cylinder when the level indicator indicates a desired level in the sample cylinder to isolate the sample cylinder.

12. The method for collecting a sample of claim 11, wherein the fluid is LPG.

* * * * *